(12) United States Patent
Yasuda et al.

(10) Patent No.: US 9,418,825 B2
(45) Date of Patent: Aug. 16, 2016

(54) METHOD AND DEVICE FOR MASS SPECTROMETRY

(71) Applicant: HITACHI HIGH-TECHNOLOGIES CORPORATION, Tokyo (JP)

(72) Inventors: Hiroyuki Yasuda, Tokyo (JP); Shinya Ito, Tokyo (JP); Akira Fujii, Tokyo (JP); Yasushi Terui, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/762,916

(22) PCT Filed: Jan. 27, 2014

(86) PCT No.: PCT/JP2014/051610
§ 371 (c)(1),
(2) Date: Jul. 23, 2015

(87) PCT Pub. No.: WO2014/119496
PCT Pub. Date: Aug. 7, 2014

(65) Prior Publication Data
US 2015/0371837 A1    Dec. 24, 2015

(30) Foreign Application Priority Data

Jan. 30, 2013  (JP) ................ 2013-014971

(51) Int. Cl.
*H01J 49/04*  (2006.01)
*H01J 49/16*  (2006.01)
*G01N 30/72*  (2006.01)

(52) U.S. Cl.
CPC .......... *H01J 49/0445* (2013.01); *G01N 30/724* (2013.01); *H01J 49/165* (2013.01)

(58) Field of Classification Search
CPC .. G01N 30/724; H01J 49/0445; H01J 49/165; H01J 49/167
See application file for complete search history.

(56) References Cited

U.S. PATENT DOCUMENTS

| 5,130,538 A | 7/1992 | Fenn et al. |
| 2003/0183757 A1 | 10/2003 | Kato |

(Continued)

FOREIGN PATENT DOCUMENTS

| JP | 62-032365 A | 2/1987 |
| JP | 62-050659 A | 3/1987 |

(Continued)

OTHER PUBLICATIONS

International Search Report of PCT/JP2014/051610.

(Continued)

Primary Examiner — Wyatt Stoffa
(74) Attorney, Agent, or Firm — Mattingly & Malur, PC (57) ABSTRACT

A mass spectrometry is equipped with a liquid specimen supply part which supplies a liquid specimen sandwiched between bubbles, an ion source part ionizes the specimen, and a mass spectrometry part which detects ions separated in accordance with mass. In particular the ion source part is configured so as to include a liquid supply tube for transporting a specimen from the liquid specimen supply part, a degassing/liquid retention part in which bubbles are removed, a spraying part which ionizes the specimen, and a high-voltage power supply part which applies a high voltage to the spraying part. The device is further characterized in that after removing the bubbles, a Taylor cone is formed from the resultant pre-solution, and the specimen is ionized thereafter. Thus, the ionization of an intended specimen is stabilized, and the measurement reproducibility is improved.

9 Claims, 10 Drawing Sheets

(56) References Cited

U.S. PATENT DOCUMENTS

| | | | | |
|---|---|---|---|---|
| 2010/0317118 | A1* | 12/2010 | Masujima | H01J 49/167 436/63 |
| 2012/0223225 | A1* | 9/2012 | Russell | H01J 49/167 250/288 |
| 2013/0181010 | A1* | 7/2013 | Ouyang | G01N 1/286 222/209 |
| 2013/0330714 | A1* | 12/2013 | Cooks | C12Q 1/04 435/5 |

FOREIGN PATENT DOCUMENTS

| | | |
|---|---|---|
| JP | 07-159415 A | 6/1995 |
| WO | 03/065405 A1 | 8/2003 |

OTHER PUBLICATIONS

Atsumu Hirabayashi, Electro Spray ni Okeru Taylor Cone no Keisei, Journal of the Textile Machinery Society of Japan, Nov. 25, 2011, pp. 657 to 661, vol. 64, No. 11.

* cited by examiner

METHOD AND DEVICE FOR MASS SPECTROMETRY

TECHNICAL FIELD

The present invention relates to a mass spectrometer.

BACKGROUND ART

A mass spectrometer is an apparatus which ionizes sample molecules by electrically charging the sample molecules, separates the generated ions according to their mass-to-charge ratios using an electric field or a magnetic field and measures the amounts thereof as electric current values with a detector. A mass spectrometer is highly sensitive and is superior in quantification performance and identification capability to the conventional analyzers. In recent years, peptide analysis and metabolite analysis, which replace genomic analysis, have received attention in the field of life science, and the effectiveness of a mass spectrometer, which is highly sensitive and has excellent identification/quantification capability, has been reassessed.

Figure 1:
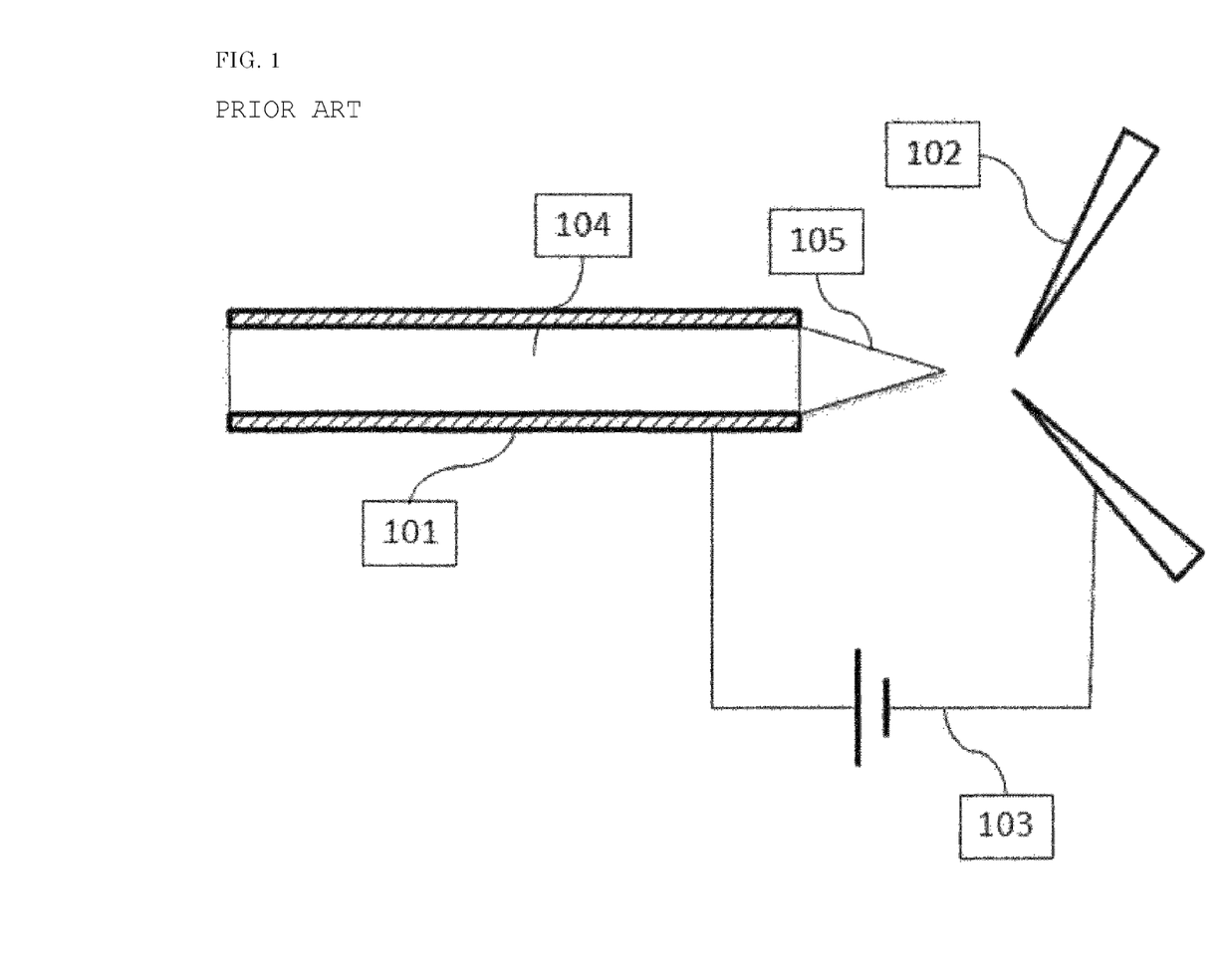

One of the ionization methods used for a mass spectrometer is electrospray ionization method (ESI method) described in PTL 1. In ESI method, a spray unit 101, a counter electrode 102 and a high voltage power supply 103 are used, and a high voltage is applied to a sample solution 104 flowing through the spray unit between the spray unit and the counter electrode to create a Taylor cone 105 and ionize the sample. The ions are detected by a mass analyzer unit provided in the downstream of the counter electrode. ESI method is soft ionization and is thus characterized by being able to ionize samples which easily detach, such as proteins, without destroying their molecular structures. Moreover, since the sample can be introduced continuously using a carrier solvent, ESI method is used for quantitative measurement and structure analysis in the field of biotechnology and the field of drug development by connecting an apparatus for separating components, such as liquid chromatograph, in the upstream of a mass spectrometer.

In general, an actual sample to be measured contains many impurities in addition to the ions to be measured. Thus, the target ions are measured with a mass spectrometer after separating the components using the analysis column of liquid chromatograph. However, when the sample used is a standard substance which does not contain any impurities or when the sample is treated in advance to remove impurities, flow injection analysis method (FIA method) without passing the sample through an analysis column is often employed. In FIA method, a sample is injected into a carrier flow path and introduced to a mass spectrometer by a feeding pump. Advantages of FIA method are that optimization and equilibration of the analysis column are not required because no analysis column is used and that the measurement is thus easy. Also, the solvent used is not restricted by the analysis column, and solvents suitable for ionization, such as methanol, can be used.

An example application of FIA method is the method of PTL 1 and PTL 2. In this method, which involves liquid chromatograph using FIA method, the sample is interposed between bubbles, and thus the loss of the sample during the sample injection can be reduced. Moreover, because the sample diffusion in the flow path can be prevented during the process of sending the solution to the detector such as an ultraviolet spectrophotometer, the S/N ratio is excellent. This method is referred to as sandwich method below.

CITATION LIST

Patent Literature

PTL 1: U.S. Pat. No. 5,130,538
PTL 2: JP-A-62-50659
PTL 3: JP-A-7-159415

SUMMARY OF INVENTION

Technical Problem

However, the signal becomes unstable when a mass spectrometer is used as a detector because bubbles are introduced when the sample is ionized by the ionization unit of the mass spectrometer. There is a fault when the signal is unstable since the measurement accuracy required for quantitative measurement decreases. The decrease is remarkable especially near the lower detection limit.

Ionization becomes unstable because the Taylor cone which is formed at the spray end of the ionization unit disappears or its shape becomes unstable. The shape of the Taylor cone can no longer be maintained when bubbles are introduced, and ionization stops or becomes unstable.

Solution to Problem

In order to solve the above problems, the invention is constituted as described in the claims.

Figure 2:
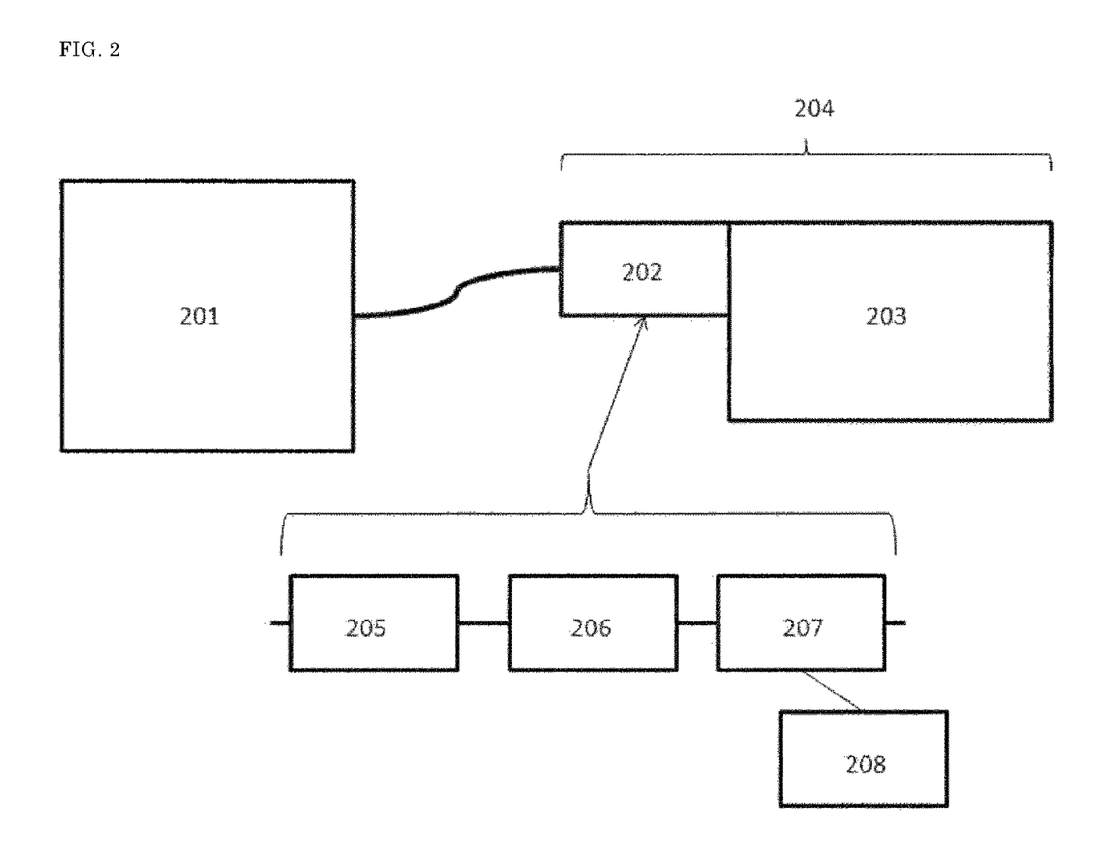

A specific example is a mass spectrometer 204 which has a sample-feeding unit 201 for interposing a sample between bubbles and feeding the sample, an ion source unit 202 for ionizing the sample and a mass analyzer unit 203 for separating the ions generated by the ion source according to the masses and detecting the ions: and which is characterized in that the ion source unit 202 contains a solution-sending pipe 205 which is a pipe for transporting the sample from the sample-feeding unit 201, a deaeration solution storage unit 206 for removing the bubbles, a spray unit 207 for ionizing the sample and a high voltage power supply unit 208 for applying a high voltage to the spray unit and that a Taylor cone is formed with a solvent after removing a bubble and the sample is ionized.

Advantageous Effects of Invention

The reproducibility of measurement improves because the target sample is ionized stably.

BRIEF DESCRIPTION OF DRAWINGS

FIG. 1 A schematic diagram of ESI method
FIG. 2 A schematic diagram of the invention
FIG. 3 First Example of the invention
FIG. 4 A flow chart for carrying out the invention
FIG. 5 A schematic diagram showing each step of the invention
FIG. 6 Second Example of the invention (horizontal type)
FIG. 7 Second Example of the invention (vertical type)
FIG. 8 Third Example of the invention
FIG. 9 Fourth Example of the invention
FIG. 10 Fourth Example of the invention (assisted with a gas)

DESCRIPTION OF EMBODIMENTS

Embodiments of the invention are explained in detail below using the attached Drawings, but the invention is not limited to the embodiments.

Example 1

First, the structure of the embodiment is explained.

Figure 3:
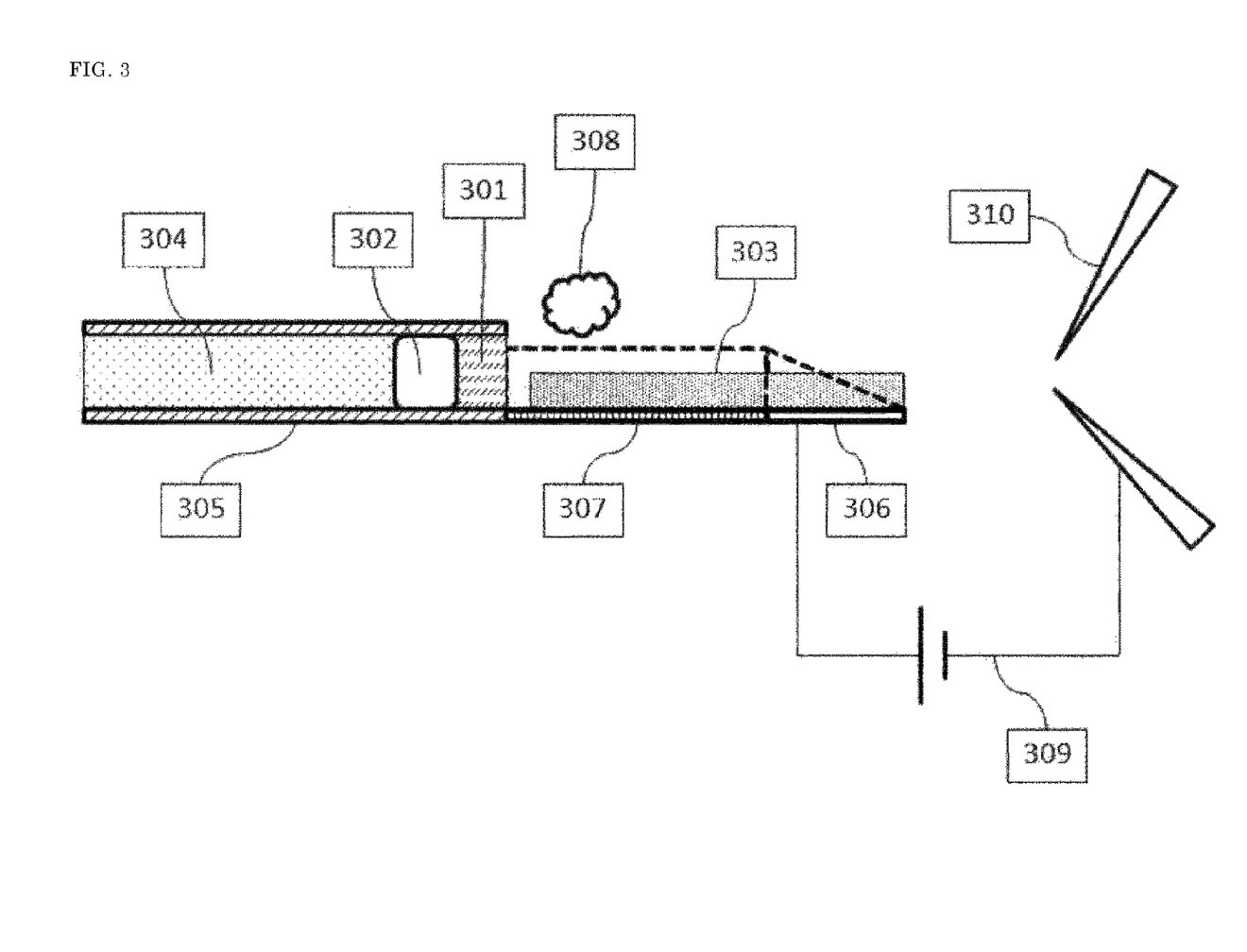

FIG. 3 is a schematic diagram of the ion source unit of the mass spectrometer according to the invention. A sample solution 301 fed from a sample-feeding unit is sandwiched by bubbles 302 from the front and the back by sandwich method. There is a pre-solution 303 which stabilizes ionization in front of the front bubble. The sample solution 301 is pushed out by a carrier solvent 304 fed from the sample-feeding unit while the diffusion is reduced and introduced into the ion source unit. In the ion source unit, the sample solution 301 is sent through a solution-sending pipe 305 having an inside diameter of about 0.05 to 0.5 mm to a spray unit 306 at the end. A deaeration solution storage unit 307 is between the solution-sending pipe and the spray unit, and since the deaeration solution storage unit 307 is atmospherically open, bubbles can be removed (308) and the solution can be stored. The section of the deaeration solution storage unit has the shape of the letter "U" or a square shape, and a liquid can be stored temporarily while being open atmospherically. Although the spray unit 306 shown in the figure is atmospherically open and has a sharp shape, the spray unit 306 may be a pipe and it has a structure which enables ESI method by applying a high voltage between the spray unit 306 and a counter electrode 310 with a high voltage power supply 309.

Figure 4:
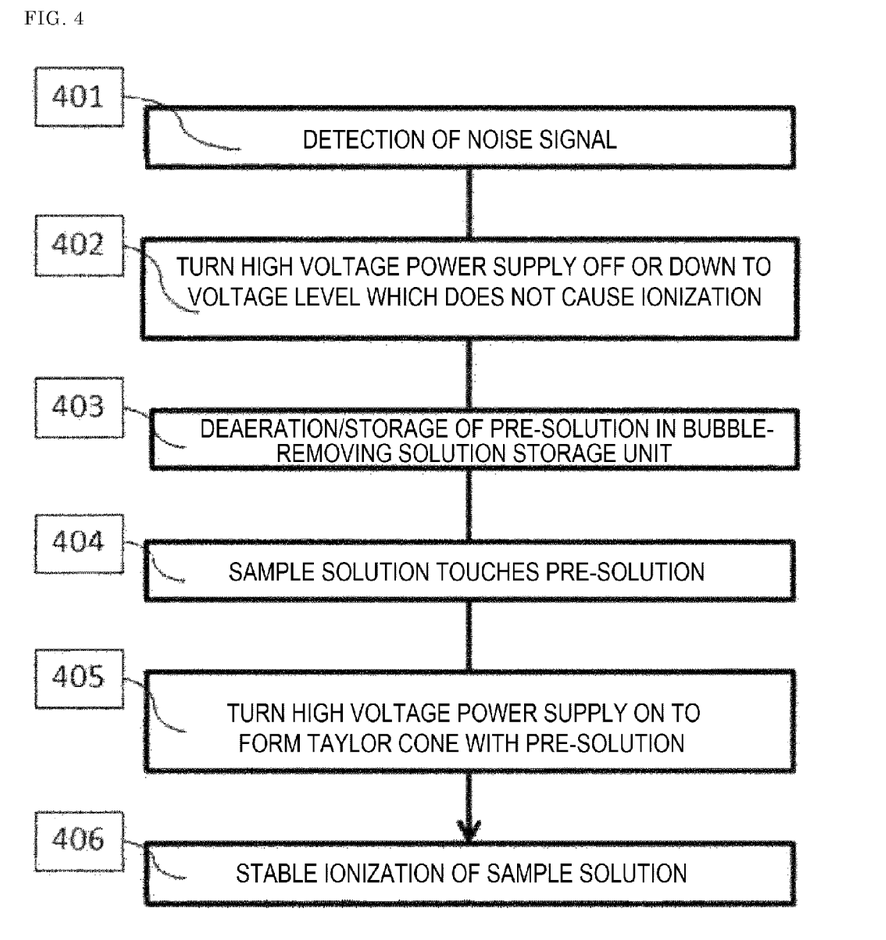
Figure 5:
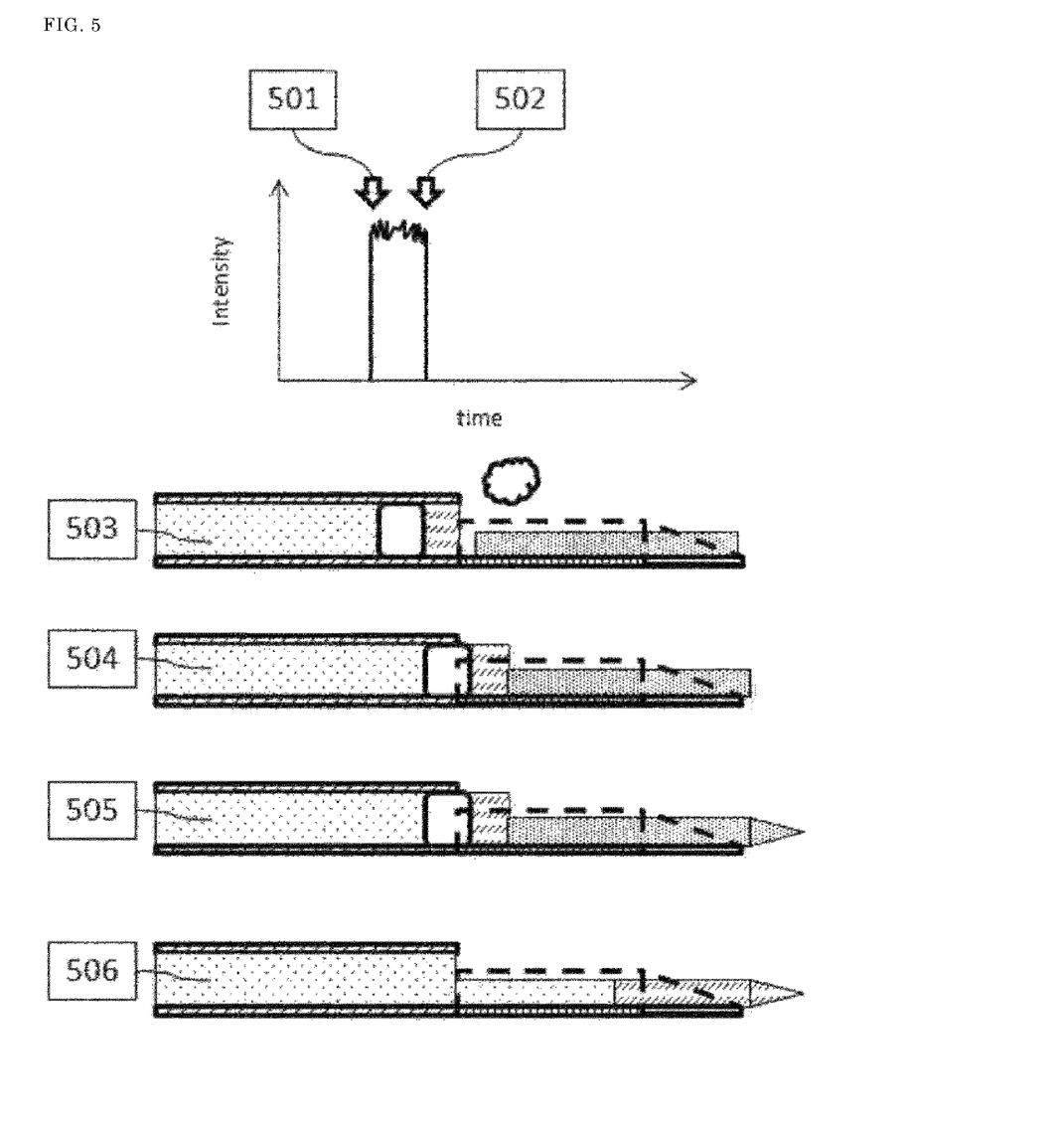

Next, the deaeration and ionization processes in the invention are explained. A flow chart of the invention is shown in FIG. 4, and a schematic diagram showing each step is shown in FIG. 5. A high voltage is applied to feed the sample solution from a solution-feeding unit. When the pre-solution reaches the end of the spray unit, the components in the pre-solution are ionized, and a signal is detected by a mass analyzer unit (401, 501). This signal is the trigger for stopping ionization (402, 502). Specifically, the high voltage power supply which applies the high voltage to the spray unit is turned off or down to the voltage level which does not cause ionization. As a result, the Taylor cone at the end of the spray unit disappears (403, 503), and the flow of the pre-solution stops. Because the solution-feeding unit continues feeding the carrier solvent at this point, the bubble in front of the sample solution reaches the deaeration solution storage unit and is released to the air. When the bubble is released, a space is formed between the pre-solution and the sample solution. Because the solution-feeding unit further continues feeding the solvent, the sample solution is pushed out and touches the pre-solution (404, 504). Then, the high voltage power supply is turned on to resume ionization, and a Taylor cone is formed with the pre-solution (409, 405, 505). After this, the sample solution reaches the spray unit, and the sample is thus ionized while keeping the Taylor cone stable (406, 506).

With the structure and the processes, the sample solution can be ionized using a stable Taylor cone. Therefore, the measurement signal stabilizes, and the reproducibility of quantitative measurement improves.

Example 2

Figure 6:
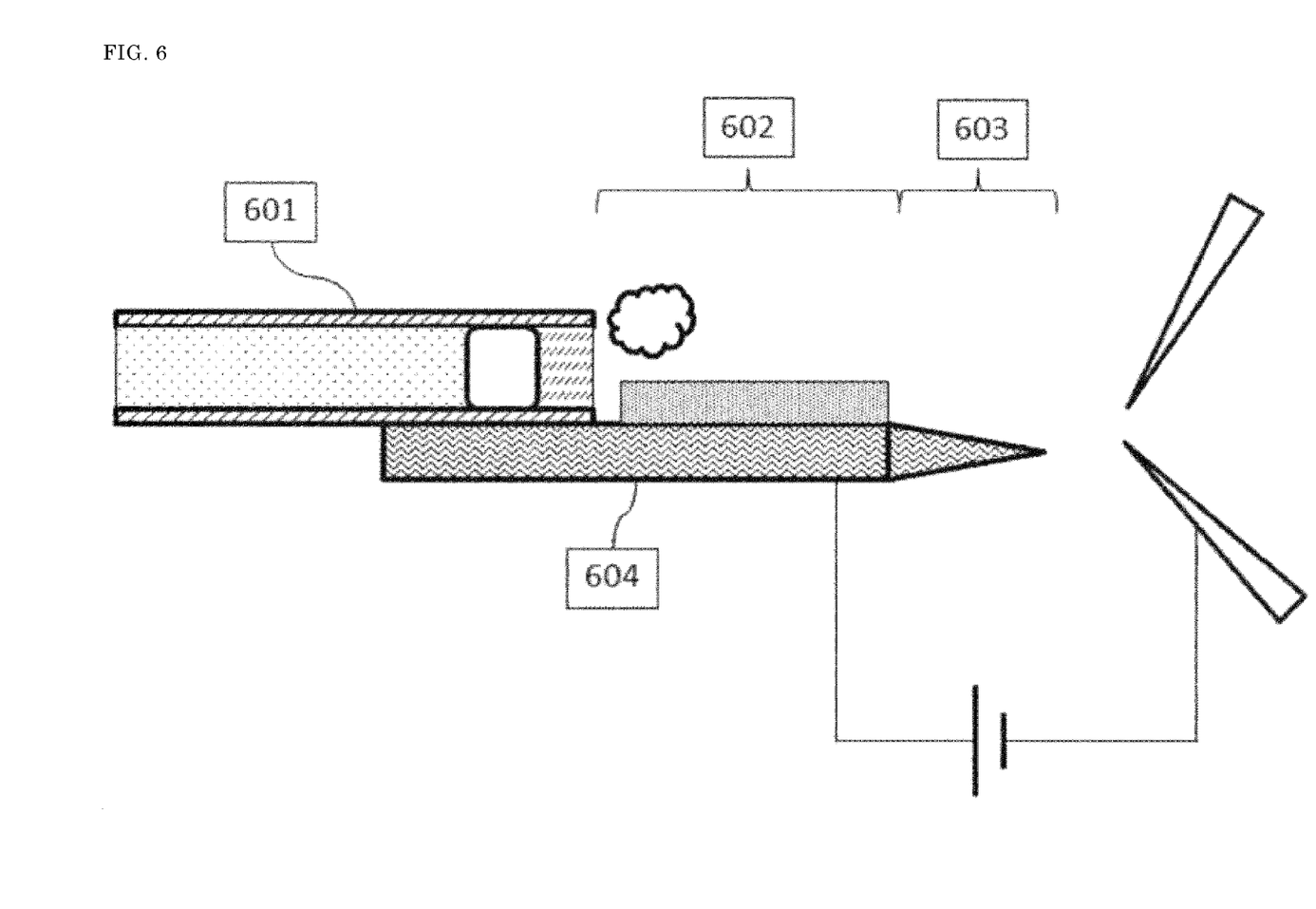

Next, the second Example is shown in FIG. 6. The second Example contains a solution-sending pipe, a deaeration solution storage unit and a spray unit like the first Example, but the deaeration solution storage unit and the spray unit are formed with one needle 604. The needle is brought into contact with the solution-sending pipe, and the sample solution including bubbles fed from the sample-feeding unit is sent onto the needle. The surface of the needle is atmospherically open, and the bubbles are thus removed. On the other hand, the solution moves on the surface of the needle due to the surface tension and reaches the point of the needle. The point of the needle is sharp, and when the solution reaches the point, a Taylor cone is formed by a high voltage and the sample is ionized.

Figure 7:
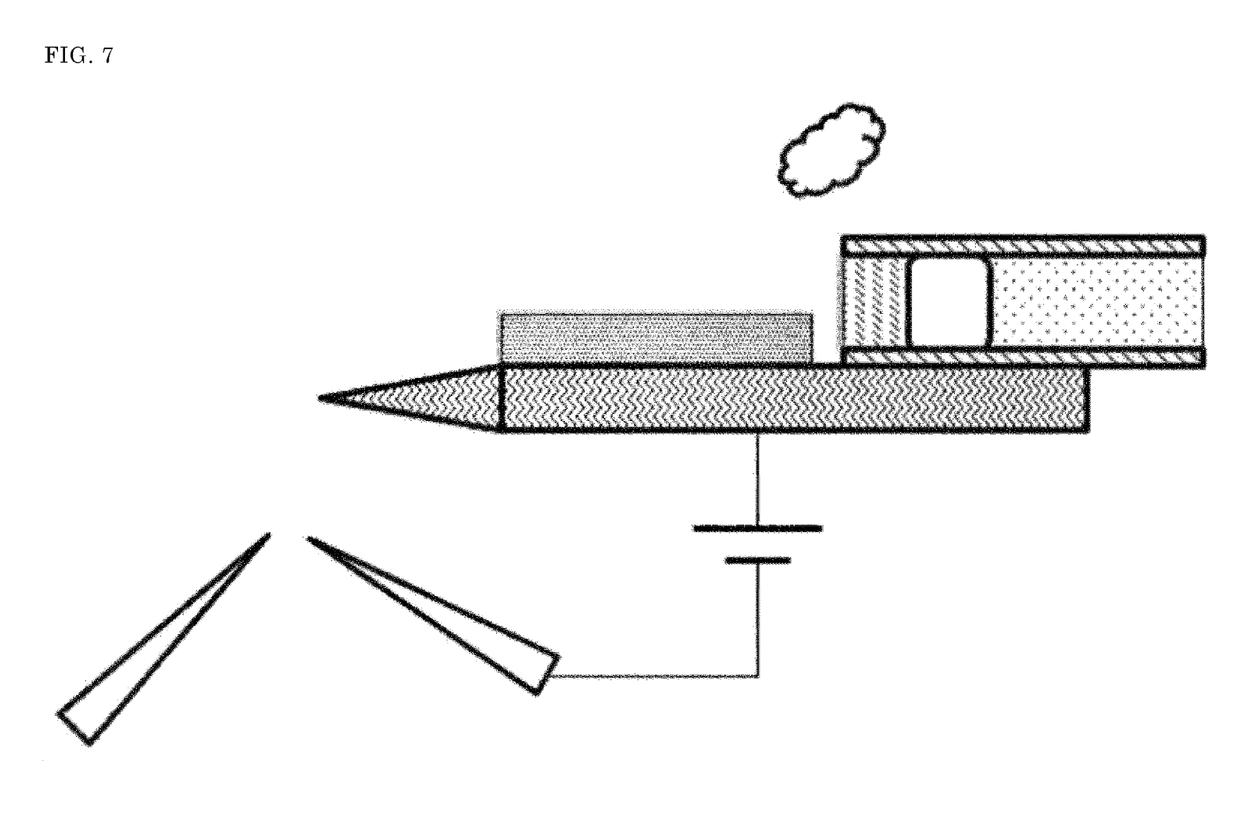

In FIG. 6, the solution is sent in the horizontal direction, but the direction may be vertical as shown in FIG. 7. A vertical type prevents the counter electrode from being polluted.

Example 3

Figure 8:
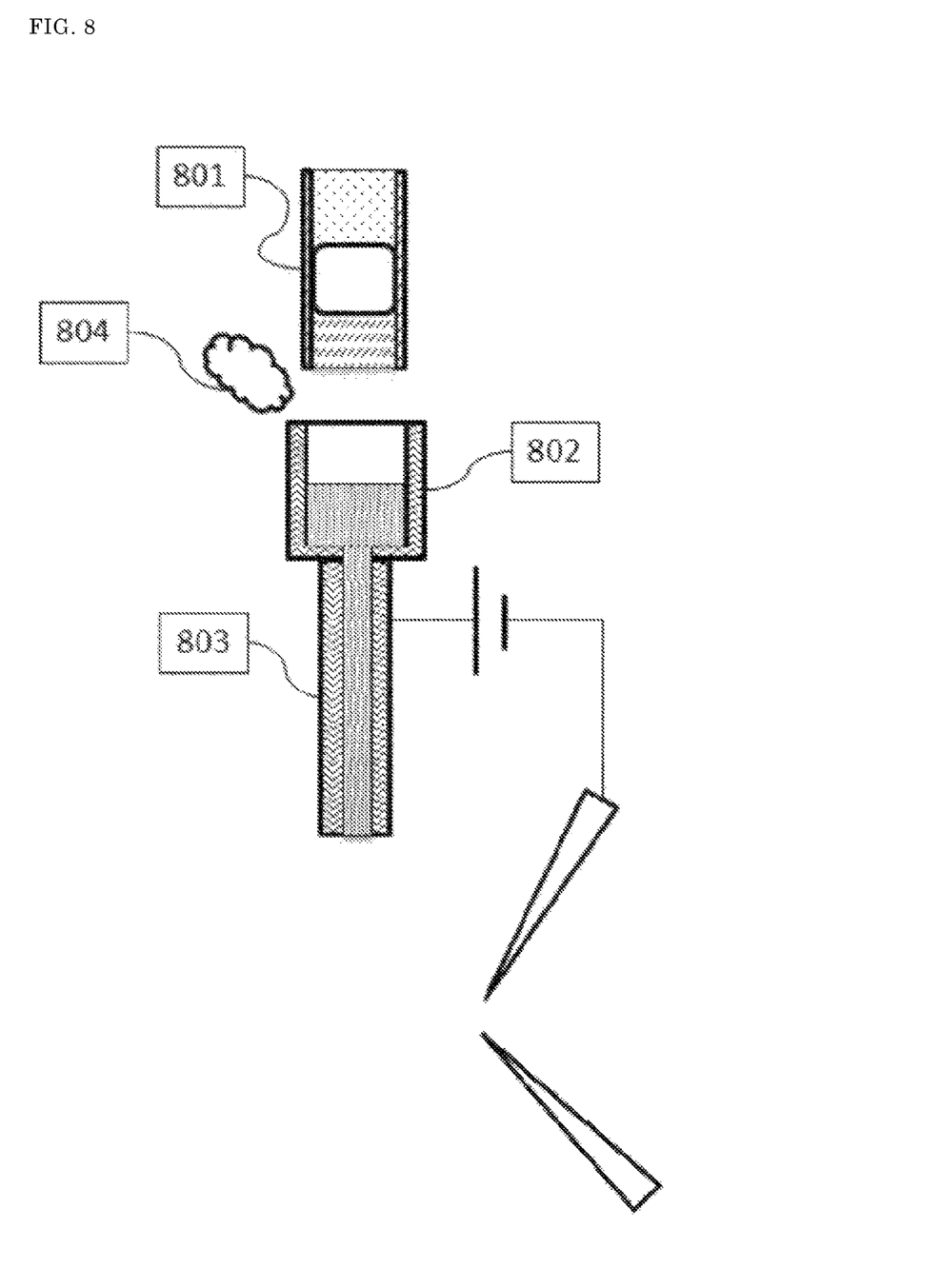

Next, the third Example is shown in FIG. 8. The third Example contains a solution-sending pipe 801, a deaeration solution storage unit 802 and a spray unit 803 like the first Example, but the deaeration solution storage unit 802 and the spray unit 803 are apart from the solution-sending pipe 801. The deaeration solution storage unit 802 is combined with the spray unit 803, and the deaeration solution storage unit 802 has a structure capable of storing a liquid. The bottom thereof has a hole which is connected to the spray unit 803 which has a pipe form extending downward. The sample solution including bubbles fed from the sample-feeding unit drops from the end of the solution-sending pipe and is stored in the deaeration solution storage unit 802. Here, because this part is atmospherically open, a bubble 804 is removed. Then, the solution reaches the end of the spray unit through the hole at the bottom, and the sample is ionized.

Example 4

Figure 9:
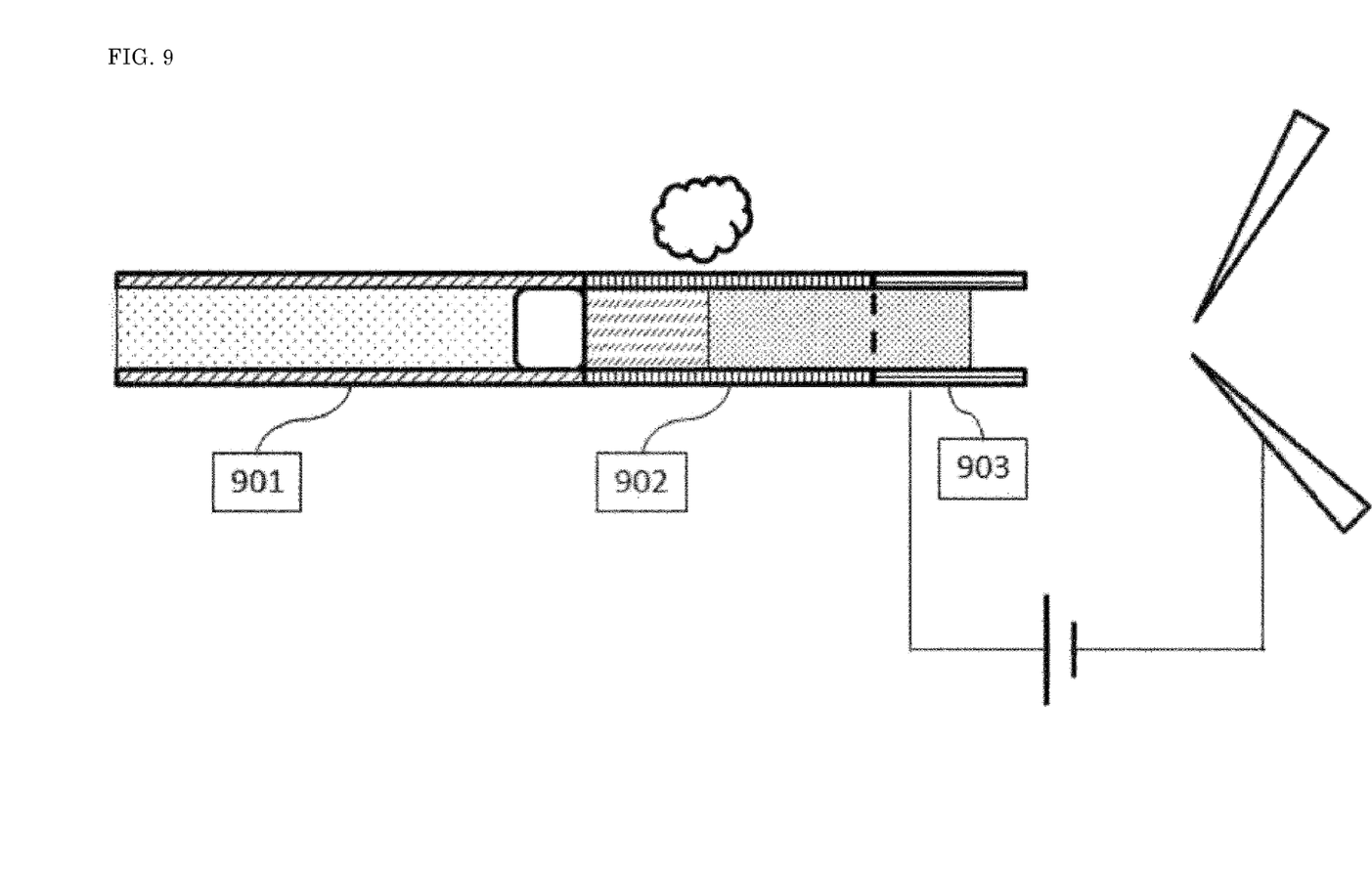

Next, the fourth Example is shown in FIG. 9. The fourth Example contains a solution-sending pipe 901, a deaeration solution storage unit 902 and a spray unit 903 like the first Example, but the deaeration solution storage unit 902 and the spray unit 903 are cylindrical pipes, and the deaeration solution storage unit 902 is made from a porous material such as a hollow fiber membrane. A porous material which has fine pores for example of 0.03 µm in size and which can separate gasses is used. In the deaeration step (403, 503) in the process of the invention shown in Example 1, the porous material selectively removes bubbles from the flow path. As a result, the structure for carrying out the invention can be simplified.

Figure 10:
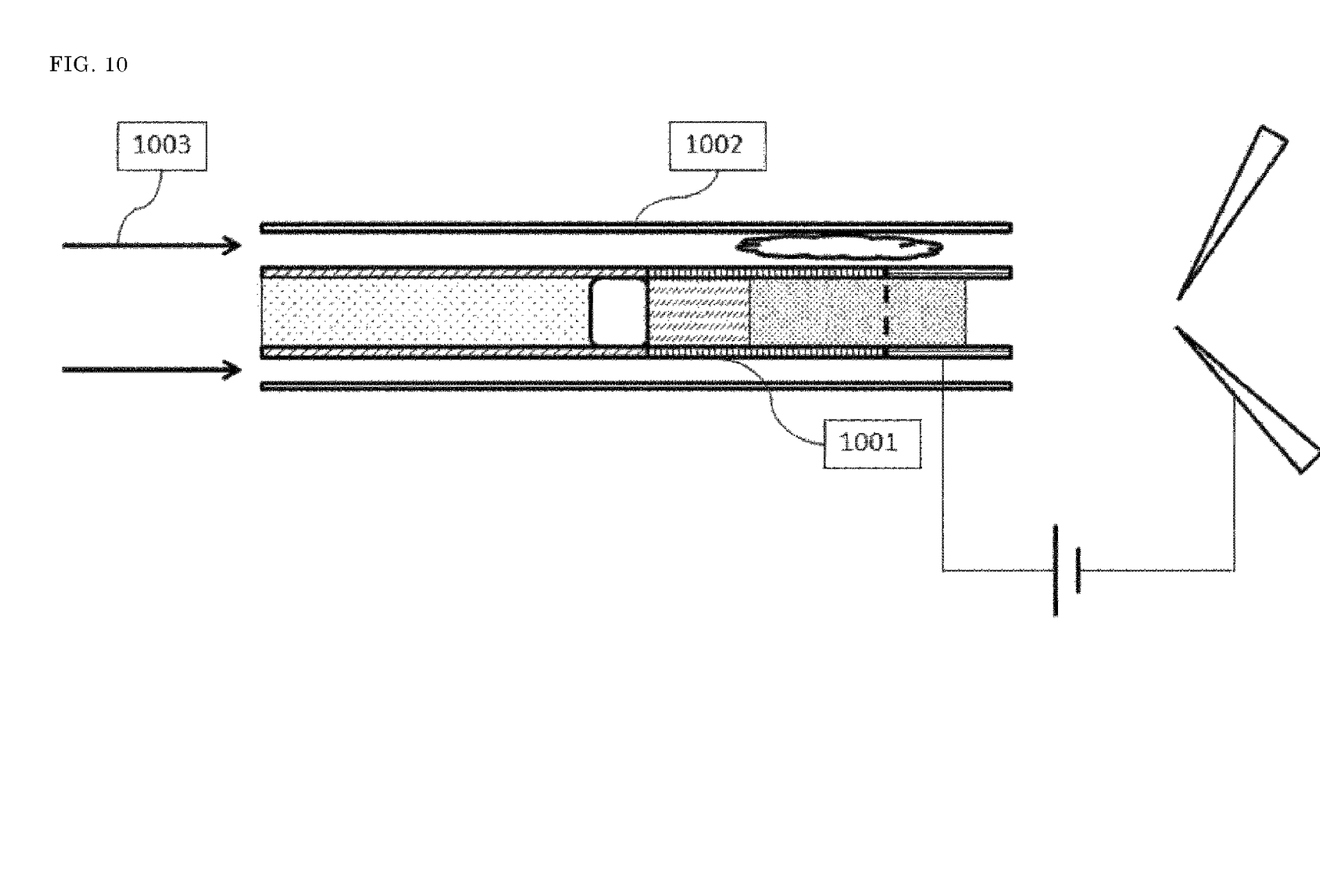

Moreover, in order to shorten the deaeration period or improve the efficiency, it is preferable that a gas flows around the porous material. A schematic diagram thereof is shown in FIG. 10. A pipe 1002 having a large diameter is placed around a deaeration solution storage unit 1001. An inert gas such as nitrogen and helium flows around the porous material (1003). The gas flow reduces the pressure around the porous material and accelerates the removal of the bubbles. In this regard, the gas flow may be the nebulizer gas flow used for assisting ionization.

REFERENCE SIGNS LIST

101: spray unit, 102: counter electrode, 103: high voltage power supply, 104: sample solution, 105: Taylor cone, 201: sample-feeding unit, 202: ion source unit, 203: mass analyzer unit, 204: mass spectrometer, 205: solution-sending pipe, 206: deaeration solution storage unit, 207: spray unit, 208: high voltage power supply unit, 301: sample solution, 302: bubble, 303: pre-solution, 304: carrier solvent, 305: solution-sending pipe, 306: spray unit, 307: deaeration solution storage unit, 308: removed bubble, 309: high voltage power supply, 310: counter electrode, 401: step of detecting noise signal, 402: step of turning high voltage power supply off, 403: deaeration and solution storage step, 404: step of bringing solutions into contact, 405: step of applying high voltage, 406: step of detecting stable signal, 501: noise signal detection in chromatograph, 502: high voltage power supply off in chromatograph, 503: schematic diagram of deaeration and solution storage step, 504: schematic diagram of step of bringing solutions into contact, 505: schematic diagram of step of applying high voltage, 506: schematic diagram of step of detecting stable signal, 601: solution-sending pipe, 602: deaeration solution storage unit, 603: spray unit, 604: needle, 801: solution-sending pipe, 802: deaeration solution storage unit, 803: spray unit, 804: removed bubble, 901: solution-sending pipe, 902: deaeration solution storage unit, 903: spray unit, 904: removed bubble, 1001: deaeration solution storage unit, 1002: pipe around deaeration solution storage unit, and 1003: gas flow for accelerating deaeration.

The invention claimed is:

1. A mass spectrometer comprising:
a sample-feeding unit for interposing a sample between bubbles and feeding the sample, an ion source unit for ionizing the sample and a mass analyzer unit for separating the ions generated by the ion source according to the masses and detecting the ions,
wherein the ion source unit comprises:
a solution-sending pipe which is a pipe for transporting the sample from the sample-feeding unit,
a deaeration solution storage unit for removing the bubbles,
a spray unit configured to ionize the sample and a solvent, and
a high voltage power supply unit configured to apply a high voltage to the spray unit thereby forming a Taylor cone of the solvent on one end of the spray unit.

2. The mass spectrometer according to claim 1, wherein the high voltage power supply is configured to turn on and off based on a signal from the mass analyzer unit.

3. The mass spectrometer according to claim 1, wherein the deaeration solution storage unit is atmospherically open and has a plate shape.

4. The mass spectrometer according to claim 1, wherein the deaeration solution storage unit and the spray unit comprise a needle.

5. The mass spectrometer according to claim 1, wherein the deaeration solution storage unit and the spray unit are apart from the solution-sending pipe.

6. The mass spectrometer according to claim 1, wherein the material of the deaeration solution storage unit is a porous material for deaeration.

7. The mass spectrometer according to claim 4, wherein a deaeration efficiency is increased by letting a gas flow around the deaeration solution storage unit.

8. A method of mass spectrometry of a mass spectrometer having a sample-feeding unit for interposing a sample between bubbles and feeding the sample, an ion source unit, a mass analyzer unit, wherein the ion source unit has a solution-sending pipe which is a pipe for transporting the sample from the sample-feeding unit, a deaeration solution storage unit, a spray unit configured, and a high voltage power supply unit, the method comprising:
feeding the sample interposed between the air bubbles through the solution-sending pipe to the deaeration solution storage unit;
removing an air bubble of the air bubbles when the air bubble is in the deaeration solution storage unit;
applying a high voltage to the spray unit from the high voltage power supply unit to form a Taylor cone with a solvent;
ionizing the sample while maintaining the Taylor cone; and
separating the ions generated by ionizing the sample according to the masses and detecting the ions, by the mass analyzer unit.

9. The method of mass spectrometry according to claim 8, further comprising:
before removing the air bubble, applying a high voltage to the spray unit from the high voltage power supply;
stopping the voltage applied to the spray unit by turning the high voltage power supply off based on a signal from the mass analyzer unit;
removing the air bubble; and
applying the high voltage to the spray unit from the high voltage power supply unit to form the Taylor cone with the solvent.

* * * * *